United States Patent
Sato et al.

(10) Patent No.: US 11,618,739 B2
(45) Date of Patent: Apr. 4, 2023

(54) METHOD OF PRODUCING ETHYLENE OXIDE AND ETHYLENE GLYCOL

(71) Applicant: NIPPON SHOKUBAI CO., LTD., Osaka (JP)

(72) Inventors: Shota Sato, Kanagawa (JP); Hideto Suzuki, Kanagawa (JP); Daisuke Higashioka, Kanagawa (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 17/266,564

(22) PCT Filed: Aug. 9, 2019

(86) PCT No.: PCT/JP2019/031773
§ 371 (c)(1),
(2) Date: Feb. 5, 2021

(87) PCT Pub. No.: WO2020/032279
PCT Pub. Date: Feb. 13, 2020

(65) Prior Publication Data
US 2021/0309624 A1    Oct. 7, 2021

(30) Foreign Application Priority Data

Aug. 10, 2018 (JP) .............................. JP2018-151727

(51) Int. Cl.
*C07D 301/10* (2006.01)
*C07C 29/04* (2006.01)
(Continued)

(52) U.S. Cl.
CPC ............ *C07D 301/10* (2013.01); *C07C 29/04* (2013.01); *C07C 29/84* (2013.01); *C07D 301/32* (2013.01)

(58) Field of Classification Search
CPC .... C07D 301/10; C07D 301/32; B01D 3/141; B01D 3/28; C07C 29/80; C07C 29/106; C07C 29/04
(Continued)

(56) References Cited

U.S. PATENT DOCUMENTS

| 4,622,104 A | 11/1986 | Neel et al. |
| 2005/0240037 A1 | 10/2005 | Bassler et al. |
| 2016/0052900 A1 | 2/2016 | Watanabe et al. |

FOREIGN PATENT DOCUMENTS

| CN | 104370704 A | 2/2015 |
| EP | 2980081 A1 | 2/2016 |

(Continued)

OTHER PUBLICATIONS

Wikipedia, 1,4-dioxane, Oct. 2017, p. 1-8. (Year: 2017).*

(Continued)

*Primary Examiner* — Taylor V Oh
(74) *Attorney, Agent, or Firm* — Lucas & Mercanti, LLP (57) ABSTRACT

There is provided a method of producing ethylene oxide and ethylene glycol capable of reducing a concentration in discharged water of 1,4-dioxane contained generated in a step of producing ethylene oxide and ethylene glycol.

A method of producing ethylene oxide and ethylene glycol includes a predetermined step of producing ethylene oxide, and a step of extracting a part of a column bottom liquid of an ethylene oxide stripping column in the step of producing ethylene oxide and supplying the extracted column bottom liquid to a by-produced ethylene glycol concentration column, concentrating ethylene glycol produced as a by-product in the step of producing ethylene oxide, and distilling and separating 1,4-dioxane produced as a by-product in the (Continued)

step of producing ethylene oxide, wherein the by-produced ethylene glycol concentration column is a divided wall distillation column.

3 Claims, 4 Drawing Sheets

(51) Int. Cl.
*C07C 29/84* (2006.01)
*C07D 301/32* (2006.01)

(58) Field of Classification Search
USPC .......................................................... 549/538
See application file for complete search history.

(56) References Cited

FOREIGN PATENT DOCUMENTS

| | | |
|---|---|---|
| JP | S62-16472 A | 1/1987 |
| JP | S62-103072 A | 5/1987 |
| JP | S63-170206 A | 7/1988 |
| JP | H09-299701 A | 11/1997 |
| JP | 2011-213663 A | 10/2011 |
| WO | 2014/157699 A1 | 10/2014 |

OTHER PUBLICATIONS

PCT, International Search Report for the corresponding patent application No. PCT/JP2019/031773, dated Oct. 29, 2019, with English translation.

PCT, Written Opinion of the International Searching Authority for the corresponding patent application No. PCT/JP2019/031773, dated Oct. 29, 2019 (English translation not available).

"Chemical process," edited by The Society of Chemical Engineers, 1998, pp. 121-128, Tokyo, Kagaku Dojin, with partial English translation.

EPO, Extended European Search Report for the corresponding European patent application No. 19848651.6, dated Sep. 2, 2021.

EPO, Office Action for the corresponding European patent application No. 19848651.6, dated Jul. 5, 2022.

Office Action dated Oct. 27, 2022 for the corresponding Chinese patent application No. 201980053680.4, with English translation.

* cited by examiner

METHOD OF PRODUCING ETHYLENE OXIDE AND ETHYLENE GLYCOL

CROSS REFERENCE TO RELATED APPLICATION

This application is a 371 of PCT/JP2019/031773 filed on Aug. 9, 2019 which, in turn, claimed the priority of Japanese patent application No. 2018-151727 filed on Aug. 10, 2018, both applications are incorporated herein by reference.

TECHNICAL FIELD

The present invention relates to a method of producing ethylene oxide and ethylene glycol. cl BACKGROUND ART Ethylene oxide is today produced by catalytic gas phase oxidation of ethylene using a molecular oxygen-containing gas in the presence of a silver catalyst. In addition, an outline of a purification method in a process for producing ethylene oxide is as follows (for example, see Patent Literature 1).

First, ethylene and a molecular oxygen-containing gas are subjected to catalytic gas phase oxidation on a silver catalyst to obtain a reaction product gas containing ethylene oxide (reaction step). Subsequently, the resulting reaction product gas is introduced into an ethylene oxide absorption column, the reaction product gas is brought into contact with an absorption liquid mainly containing water, and ethylene oxide is recovered as an aqueous solution (absorption step). Subsequently, the recovered ethylene oxide aqueous solution is fed to a purification system of ethylene oxide to obtain high-purity ethylene oxide through several stages. The ethylene oxide purification system usually includes a stripping step, a dehydration step, a light fraction separation step, a heavy fraction separation (purification) step, and the like.

As described above, the process for producing ethylene oxide includes the stripping step of stripping the resultant obtained through the absorption step of absorbing the reaction product gas containing ethylene oxide and generated in the reaction step in the absorption liquid. Here, in order to prevent impurities from accumulating in the absorption liquid in the absorption step and the stripping step, the process for producing ethylene oxide usually includes a step of extracting a part of the absorption liquid (for example, see Patent Literature 1). Since a large amount of ethylene glycol produced as a by-product (hereinafter, by-produced ethylene glycol) is contained in the extracted absorption liquid, the process for producing ethylene oxide further includes an ethylene glycol concentration step of recovering and concentrating the by-produced ethylene glycol. On the other hand, 1,4-dioxane, which is an impurity, also produced as a by-product is contained in discharged water and discharged to the outside of the system. In addition, a treatment facility for carbon dioxide ($CO_2$) produced as a by-product in an ethylene oxide reaction step is usually also installed (for example, see Non-Patent Literature 1); however, discharged water containing 1,4-dioxane is also generated from the treatment facility for $CO_2$.

It is considered that 1,4-dioxane is difficult to be decomposed and removed in the environment, is acutely toxic to animals or irritating to humans, and may cause damage to organs. Therefore, in the process for producing ethylene oxide and ethylene glycol, for example, a method in which 1,4-dioxane produced as a by-product is separated by distillation, the separated 1,4-dioxane is diluted with a large amount of water, the diluted 1,4-dioxane is introduced into an activated sludge facility as discharged water, and a treatment with sludge bacteria is performed, a method of adsorbing 1,4-dioxane produced as a by-product on activated carbon, or the like, is adopted.

However, since 1,4-dioxane is a biologically hardly degradable substance, 1,4-dioxane may be not sufficiently removed in an activated sludge method, an activated carbon adsorption method, or the like used in a discharged water treatment facility according to the related art. In the method of performing the treatment with sludge bacteria as described above, when a large amount of 1,4-dioxane is generated, a processing capacity of the activated sludge may be insufficient. Therefore, in the process for producing ethylene oxide and ethylene glycol, an effective method of treating 1,4-dioxane has not been established.

Recently, environmental standards have been strengthened based on the accumulation of the knowledge on a protection of human health from 1,4-dioxane and the like, and a general discharged water standard in which the acceptable limit of 1,4-dioxane is set to 0.5 mg/L has been set (enforced on May 25 in 2012). Ethylene oxide and ethylene glycol producing industries where it is difficult to immediately comply with the standard are in a situation in which a provisional discharged water standard is set for a period of 2 to 3 years from May 25, 2015, and thereafter, a general discharged water standard is applied. Therefore, a method of simply and more efficiently treating 1,4-dioxane is required.

CITATION LIST

Patent Literature
    Patent Literature 1: JP 62-103072 A
Non-Patent Literature
    Non-Patent Literature 1: "Chemical process" pp. 121 to 128, edited by The Society of Chemical Engineers (Tokyo Kagaku Dojin, 1998)

SUMMARY OF INVENTION

Technical Problem

As a technology for removing 1,4-dioxane, an ozone treatment, or an accelerated oxidation treatment such as a combination of an ozone treatment and a hydrogen peroxide treatment, or the like is usually known, in addition to the activated sludge method or the activated carbon adsorption method. However, in these treatment methods, under a condition in which organic matters are present in addition to 1,4-dioxane such as discharged water generated in the ethylene glycol concentration step, the organic matters are also decomposed. Therefore, an ozone amount or chemical feeding amount required is increased, and a processing cost increases.

In addition, it is possible to separate 1,4-dioxane by distilling the discharged water generated in the ethylene glycol concentration step, but in this case, a new facility equipped with not only a column body but also auxiliary equipment is required, and a construction cost or an installation area increases. In addition, in order to separate 1,4-dioxane from the discharged water generated in the ethylene glycol concentration step, for example, a heating source such as steam or the like is required, and thus, a processing cost also increases. In addition, although bacteria having an excellent 1,4-dioxane-degrading ability have been reported (JP 2018-57356 A), it has not been applied to the activated sludge method or the activated carbon adsorption method used in the discharged water treatment facility according to the related art, from the viewpoint of quantitativity or a stable treatment.

Accordingly, an object of the present invention is to provide a method of producing ethylene oxide and ethylene glycol capable of reducing a concentration in discharged water of 1,4-dioxane generated in a step of producing ethylene oxide and ethylene glycol, to a new discharged water standard value (0.5 mg/L) or less.

Solution to Problem

The present inventors have conducted intensive studies to reduce a concentration in discharged water of 1,4-dioxane generated in a process for producing ethylene oxide. As a result, the present inventors found that the above problems can be solved by using a divided wall distillation column as a by-produced ethylene glycol concentration column, thereby completing the present invention.

That is, an embodiment of the present invention relates to a method of producing ethylene oxide and ethylene glycol. The production method includes: a step of producing ethylene oxide, including: supplying, to an ethylene oxide absorption column, a reaction product gas containing ethylene oxide and generated in an ethylene oxidation reaction step in which ethylene is subjected to catalytic gas phase oxidation using a molecular oxygen-containing gas in the presence of a silver catalyst; bringing the reaction product gas into contact with an absorption liquid supplied to the ethylene oxide absorption column; supplying a column bottom liquid of the ethylene oxide absorption column, which contains ethylene oxide, to an ethylene oxide stripping column; and obtaining steam containing ethylene oxide from a column top portion of the ethylene oxide stripping column by heating a column bottom portion of the ethylene oxide stripping column; and a step of extracting a part of a column bottom liquid of the ethylene oxide stripping column and supplying the extracted column bottom liquid to a by-produced ethylene glycol concentration column, concentrating ethylene glycol produced as a by-product in the step of producing ethylene oxide, and distilling and separating 1,4-dioxane produced as a by-product in the step of producing ethylene oxide. In the production method according to the present embodiment, it is characterized in that the by-produced ethylene glycol concentration column is a divided wall distillation column.

DESCRIPTION OF EMBODIMENTS

According to an embodiment of the present invention, there is provided a method of producing ethylene oxide and ethylene glycol, the method including:

a step of producing ethylene oxide, including supplying, to an ethylene oxide absorption column, a reaction product gas containing ethylene oxide and generated in an ethylene oxidation reaction step in which ethylene is subjected to catalytic gas phase oxidation using a molecular oxygen-containing gas in the presence of a silver catalyst, bringing the reaction product gas into contact with an absorption liquid supplied to the ethylene oxide absorption column, supplying a column bottom liquid of the ethylene oxide absorption column, which contains ethylene oxide, to an ethylene oxide stripping column, and obtaining steam containing ethylene oxide from a column top portion of the ethylene oxide stripping column by heating a column bottom portion of the ethylene oxide stripping column; and a step of extracting a part of a column bottom liquid of the ethylene oxide stripping column and supplying the extracted column bottom liquid to a by-produced ethylene glycol concentration column, concentrating ethylene glycol produced as a by-product in the step of producing ethylene oxide, and distilling and separating 1,4-dioxane produced as a by-product in the step of producing ethylene oxide, in which the by-produced ethylene glycol concentration column is a divided wall distillation column.

According to the present invention, when 1,4-dioxane produced as a by-product in a process for producing ethylene oxide is separated in the step of concentrating ethylene glycol simultaneously produced as a by-product, the 1,4-dioxane can be efficiently separated and removed by using the divided wall distillation column. As a result, it is possible to reduce a concentration of 1,4-dioxane in discharged water discharged in a process for producing ethylene oxide and ethylene glycol.

Hereinafter, specific embodiments for implementing the present invention will be described in detail with reference to the drawings. However, the technical scope of the present invention should be determined based on the description of claims, and is not limited only to the following embodiments.

<<Reaction System>>

First, a system of producing ethylene oxide by an oxidation reaction of ethylene (hereinafter, also simply referred to as "reaction system") will be described with reference to FIG. 1. The process for producing ethylene oxide illustrated in FIG. 1 is roughly divided into four systems of a reaction system, a carbon dioxide gas system, a purification system, and an ethylene glycol system.

The term "reaction product gas containing ethylene oxide" used in the present invention may be produced in a step of subjecting ethylene to catalytic gas phase oxidation using a molecular oxygen-containing gas in the presence of a silver catalyst (hereinafter, also referred to as an "ethylene oxidation reaction step"). The technology itself of the catalytic gas phase oxidation reaction is widely known, and the knowledge known in the related art can be appropriately referred to in order to implement the present invention. Note that specific embodiments such as a composition of the reaction product gas and the like are not particularly limited. As an example, the reaction product gas usually contains, in addition to 0.5 to 5 vol % of ethylene oxide, unreacted oxygen, unreacted ethylene, generated water, a gas such as carbon dioxide, nitrogen, argon, methane, ethane, or the like, aldehydes such as formaldehyde, acetaldehyde, and the like, and a small amount of an organic acid such as acetic acid or the like.

Figure 1:
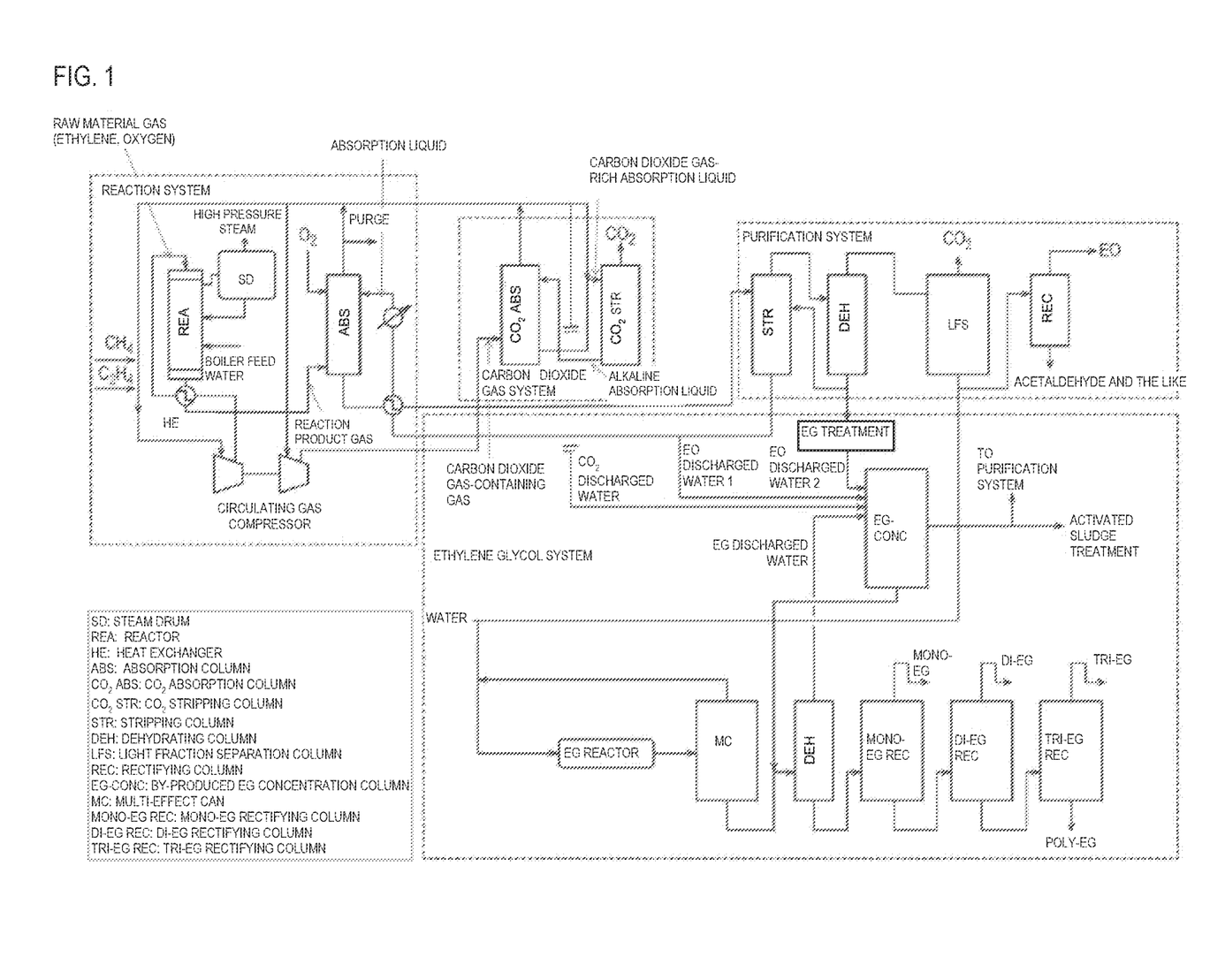
FIG. 1 is a block diagram illustrating a configuration example of a production process in which a method of producing ethylene oxide and ethylene glycol according to an embodiment of the present invention is performed.

Referring to FIG. 1, first, a pressure of a raw material gas containing ethylene or molecular oxygen is increased by a circulating gas compressor, and then the raw material gas is heated by a heat exchanger and supplied to an ethylene oxidation reactor (reactor). The ethylene oxidation reactor is usually a multi-tubular reactor provided with many reaction tubes filled with a silver catalyst. The reaction product gas produced in the ethylene oxidation reaction step is cooled by passing through the heat exchanger, and then the cooled reaction product gas is supplied to an ethylene oxide absorption column (hereinafter, also simply referred to as an "absorption column"). Specifically, the reaction product gas is supplied from a column bottom portion of the absorption column. Meanwhile, an absorption liquid mainly containing water is supplied from a column top portion of the absorption column. By doing so, counter flow contact between a gas and a liquid is performed in the absorption column, and ethylene oxide (usually, 99 mass % or more) contained in the reaction product gas is thus absorbed in the absorption liquid. In addition to ethylene oxide, ethylene, oxygen, carbon dioxide, an inert gas (nitrogen, argon, methane, ethane, or the like), and low-boiling impurities such as formaldehyde and the like, high-boiling impurities such as acetaldehyde, acetic acid, and the like, and furthermore, 1,4-dioxane, which are produced in the ethylene oxidation reaction step, are simultaneously absorbed in substantial amounts thereof. Note that the temperature of the reaction product gas supplied to the absorption column is preferably about 20 to 80° C. In addition, a composition of the absorption liquid is not particularly limited. In addition to a liquid mainly containing water, propylene carbonate as disclosed in JP 8-127573 A may be used as an absorption liquid. In addition, an additive can be added to the absorption liquid, if necessary. Examples of the additive which can be added to the absorption liquid can include a defoaming agent and a pH adjusting agent. As the defoaming agent, any defoaming agent can be used as long as it is inactive against ethylene oxide, by-produced ethylene glycol, or the like, and has an effect of defoaming the absorption liquid. However, as a typical example thereof, a water-soluble silicone emulsion is effective due to its excellent dispersibility in the absorption liquid, excellent dilution stability, and excellent thermal stability. In addition, examples of the pH adjusting agent can include compounds which can be dissolved in the absorption liquid, such as a hydroxide, a carbonate, or the like of an alkali metal such as potassium or sodium, and potassium hydroxide or sodium hydroxide is preferred. Note that a pH of the absorption liquid is preferably 4 to 12, and more preferably 6 to 11.

As the absorption column, a plate column type or packed column type absorption column can be usually used. As an operation condition of the absorption column, a concentration of ethylene oxide in the reaction product gas is 0.5 to 5 vol %, and preferably 1.0 to 4 vol %, and an operation pressure of the absorption column is 0.2 to 4.0 MPa gauge, and preferably 1.0 to 3.0 MPa gauge. An absorption operation is more advantageous as the pressure is higher. However, a possible value thereof can be determined according to an operation pressure of the oxidation reactor. In addition, a molar flow rate ratio (L/V) of the absorption liquid to the reaction product gas is usually 0.30 to 2.00. In addition, a space linear velocity (GHSV[NTP]) of the reaction product gas in a standard state is usually 400 to 6,000 $h^{-1}$.

A gas which is not absorbed in the absorption column and contains ethylene, oxygen, carbon dioxide, an inert gas (nitrogen, argon, methane, or ethane), aldehyde, an acidic substance, and the like, is discharged from the column top portion of the absorption column through a conduit. Then, the exhaust gas is pressurized by the circulating gas compressor, and then is circulated to the ethylene oxidation reactor through a conduit. Note that details of the ethylene oxidation reaction step are as described above. Here, the ethylene oxidation reaction step is usually performed in an oxidation reactor provided with many reaction tubes filled with a silver catalyst under a pressurized condition (pressure of about 1.0 to 3.0 MPa gauge). Therefore, a pressure of the exhaust gas from the column top portion of the absorption column is increased using a pressure increasing means such as a circulating gas compressor or the like before the exhaust gas is circulated to the ethylene oxidation reaction step.

<<Carbon Dioxide Gas System>>

In a preferred embodiment, as illustrated in FIG. 1, a pressure of at least a part of the gas (carbon dioxide-containing gas) discharged from the column top portion of the absorption column is increased by a pressure increasing means such as a circulating gas compressor or the like, and the pressurized gas is supplied to a carbon dioxide gas absorption column ($CO_2$ absorption column) through a conduit. Hereinafter, a carbon dioxide gas recovery system (hereinafter, also simply referred to as a "carbon dioxide gas system") starting from introduction of a gas into the carbon dioxide gas absorption column will be described with reference to FIG. 1.

As described above, in a case where the gas discharged from the column top portion of the absorption column is pressurized and introduced into the carbon dioxide gas absorption column through a conduit, the gas pressure at this time is adjusted to about 0.5 to 4.0 MPa gauge, and the gas temperature is adjusted to about 80 to 120° C. A carbon dioxide gas stripping column ($CO_2$ stripping column) is installed at a post-stage of the carbon dioxide gas absorption column. An alkaline absorption liquid is supplied from a column bottom portion of the carbon dioxide gas stripping column to an upper portion of the carbon dioxide gas absorption column. Then, a carbon dioxide gas and a small amount of inert gas (for example, ethylene, methane, ethane, oxygen, nitrogen, argon, or the like), contained in the gas introduced into the carbon dioxide gas absorption column, are absorbed by counter flow contact with the alkaline absorption liquid. An unabsorbed gas discharged from a column top portion of the carbon dioxide gas absorption column is circulated to the conduit, is subjected to heat exchange with a gas introduced into the carbon dioxide gas absorption column described above, then is mixed with oxygen, ethylene, methane, or the like to be newly replenished, and then is circulated to the ethylene oxidation reactor. Since the temperature of the gas discharged from the column top portion of the carbon dioxide gas absorption column is reduced during the heat exchange, moisture is usually condensed in a state where a trace amount of organic matter (for example, 1,4-dioxane, ethylene glycol, or the like) is contained therein to become organic matter-containing water. The organic matter-containing water is mostly supplied to the carbon dioxide gas stripping column through a conduit, and a part of the organic matter-containing water is supplied to a by-produced ethylene glycol concentration column as $CO_2$ discharged water to prevent concentration of impurities in the carbon dioxide gas system.

The absorption liquid (carbon dioxide gas-rich absorption liquid) which has absorbed the carbon dioxide gas in the carbon dioxide gas absorption column is extracted from a column bottom portion of the carbon dioxide gas absorption column. Thereafter, the pressure thereof is adjusted to 0.01 to 0.5 MPa gauge, and the temperature thereof is adjusted to about 80 to 120° C., thereby supplying the absorption liquid to an upper portion of the carbon dioxide gas stripping column. In a liquid supply section at the upper portion of the carbon dioxide gas stripping column, the carbon dioxide gas-rich absorption liquid causes pressure flash due to a pressure difference between the carbon dioxide gas absorption column and the carbon dioxide gas stripping column. Accordingly, 10 to 80 vol % of the carbon dioxide gas and most of the inert gas in the carbon dioxide gas-rich absorption liquid are separated from the absorption liquid, and discharged as an exhaust gas from a column top portion of the carbon dioxide gas stripping column.

That is, the method according to an embodiment of the present invention further includes a carbon dioxide gas recovering step of supplying at least a part of a carbon dioxide-containing gas discharged from the column top portion of the ethylene oxide absorption column to a carbon dioxide gas absorption column, extracting a carbon dioxide gas-rich absorption liquid obtained by bringing the carbon dioxide-containing gas into contact with an absorption liquid as a column bottom liquid of the carbon dioxide gas absorption column and supplying the extracted carbon dioxide gas-rich absorption liquid to an upper portion of a carbon dioxide gas stripping column, and stripping a carbon dioxide gas from the carbon dioxide gas-rich absorption liquid and discharging the carbon dioxide gas from the column top portion of the carbon dioxide gas stripping column as an exhaust gas. Discharged water discharged from the carbon dioxide gas recovering step is supplied to the by-produced ethylene glycol concentration column.

Note that the remaining carbon dioxide gas-rich absorption liquid from which the part of the carbon dioxide gas is separated due to the pressure flash described above enters a gas-liquid contact section (not illustrated) provided below the liquid supply section, the remaining carbon dioxide gas-rich absorption liquid is subjected to counter flow contact with a gas mainly containing a carbon dioxide gas, and a part of the carbon dioxide gas and most of the other inert gases in the absorption liquid are separated from the absorption liquid. By a series of the processes in the carbon dioxide gas system, a high-purity carbon dioxide gas is obtained.

<<Purification System>>

The absorption liquid which has absorbed ethylene oxide in the ethylene oxide absorption column (absorption column) is fed to an ethylene oxide purification system (hereinafter, also simply referred to as a "purification system") as a column bottom liquid of the absorption column. Specific embodiments of the purification system are not particularly limited, but a knowledge known in the related art can be appropriately referred to. As an example, the purification system generally includes a stripping step, a dehydration step, a light fraction separation step, a heavy fraction separation (purification) step, and the like.

The column bottom liquid of the absorption column (absorption liquid) is usually heated to a temperature suitable for stripping in an ethylene oxide stripping column (hereinafter, also simply referred to as a "stripping column") in advance before being supplied to the stripping column. Specifically, the column bottom liquid of the absorption column (absorption liquid) is supplied to a heat exchanger, heat exchange with a column bottom liquid of the stripping column is performed in the heat exchanger, and the column bottom liquid of the absorption column is further heated by a heater or the like, if necessary. For example, the column bottom liquid of the absorption column (absorption liquid) is heated to a temperature of about 70 to 110° C. Preferably, the column bottom liquid of the absorption column (absorption liquid) is further supplied to a gas-liquid separation tank (not illustrated), and a light fraction gas of an inert gas partially containing ethylene oxide and water is separated in the gas-liquid separation tank and discharged through a conduit. On the other hand, a residual absorption liquid obtained by flashing the light fraction gas is supplied to an upper portion of the stripping column through a conduit.

Subsequently, the stripping column is preferably heated. By heating the stripping column, ethylene oxide contained in the absorption liquid supplied from the upper portion of the stripping column (usually 99 mass % or more thereof) is stripped and discharged from a column top portion of the stripping column through a conduit. Note that as for operation conditions of the stripping column, a column top pressure is usually 0.01 to 0.20 MPa gauge, and preferably 0.03 to 0.06 MPa gauge. The smaller the column top pressure is, the lower the temperature in the column is. As a result, production of ethylene glycol as a by-product from ethylene oxide in the column tends to be suppressed. However, ethylene oxide is a substance which is relatively easily ignitable. Therefore, usually, the operation is not performed at atmospheric pressure or lower, and is performed at a pressure a little higher than atmospheric pressure as described above, from the viewpoint of preventing a leakage of oxygen into the system. Note that as for temperature conditions of the stripping column, a column top temperature is usually 85 to 120° C., and a column bottom temperature is usually 100 to 130° C.

The residual absorption liquid obtained after stripping ethylene oxide can be extracted as the column bottom liquid of the stripping column, be supplied to an upper portion of the absorption column as the absorption liquid of the absorption column, and be circulated and used. However, in order to adjust the composition of the absorption liquid, fresh water, or if necessary, the additive described above may be supplied to the absorption column through a conduit separately provided. In addition, it is preferable that a concentration of impurities in the absorption liquid supplied to the absorption column is suppressed to constantly maintain a concentration of ethylene glycol. Therefore, a part of the absorption liquid circulating between the absorption column and the stripping column is extracted from a column bottom portion of the stripping column. Here, the column bottom liquid of the stripping column does not contain ethylene oxide substantially. Specifically, the concentration of ethylene oxide contained in the column bottom liquid is preferably 10 mass ppm or less, and more preferably 0.5 mass ppm or less. The column bottom liquid contains ethylene glycol produced in the absorption liquid as a by-product between the ethylene oxidation reaction step and the ethylene oxide stripping step. A part thereof is extracted through a conduit. The extracted liquid is supplied to the ethylene glycol concentration step for concentrating and recovering ethylene glycol contained in the extracted liquid as ethylene oxide (EO) discharged water 1 described below. Note that, because the column bottom liquid of the stripping column also contains low-boiling impurities such as formaldehyde and the like and high-boiling impurities such as acetaldehyde, acetic acid, and the like, as described above, by extracting a part of the column bottom liquid from the system, it is possible to prevent accumulation of these impurities in the absorption liquid circulated to the absorption column. In addition, 1,4-dioxane produced as a by-product in the oxidation reaction step and the absorption stripping step is contained in the partially extracted absorption liquid, but 1,4-dioxane is also discharged from the system through the ethylene glycol concentration step. On the other hand, the column bottom liquid of the stripping column which is not extracted through a conduit is cooled by heat exchange with the column bottom liquid of the absorption column by passing through the heat exchanger, and is circulated to the column top portion of the absorption column.

An ethylene oxide-containing stripped substance stripped from the column top portion of the stripping column is preferably fed to a stripping column condenser (not illustrated) through a conduit, a condensed liquid is refluxed to the column top portion of the stripping column through a conduit, and uncondensed steam is supplied to a dehydrating column through a conduit.

The ethylene oxide-containing steam (uncondensed steam) supplied to the dehydrating column comes into contact with a liquid to be refluxed through a conduit and becomes steam having a higher concentration of ethylene oxide, and a liquid having a low concentration of ethylene oxide is extracted from a column bottom.

Note that a part of a column bottom liquid of the dehydrating column is subjected to an ethylene glycolation (EG) treatment and then supplied to the ethylene glycol concentration step. An example of the EG treatment can include a step of reacting ethylene oxide with water to obtain an aqueous solution containing monoethylene glycol, diethylene glycol, triethylene glycol, tetraethylene glycol, and polyethylene glycol, and the EG treatment can be performed under the same condition as that of an EG reaction in an EG reactor described below. In addition, EO discharged water 1 described below can be used as water required for the EG treatment. Therefore, a liquid obtained by the EG treatment also contains 1,4-dioxane. The liquid is supplied to the ethylene glycol concentration step for concentrating and recovering ethylene glycol contained in the liquid as EO discharged water 2 described below. A residue of the column bottom liquid of the dehydrating column is supplied to the stripping column and circulated and used.

The ethylene oxide-containing steam discharged from a column top portion of the dehydrating column is preferably fed to a dehydrating column condenser (not illustrated) through a conduit. In this case, a part of the condensed liquid discharged from the dehydrating column condenser is refluxed to the column top portion of the dehydrating column through the conduit, and uncondensed steam (ethylene oxide-containing uncondensed gas) in the dehydrating column condenser is supplied to an ethylene oxide reabsorption column (not illustrated) through a conduit. Similarly to the absorption column described above, in the ethylene oxide reabsorption column, ethylene oxide is reabsorbed by counter flow contact with the absorption liquid. A residue of the condensed liquid from the dehydrating column condenser is supplied to a light fraction separation column through a conduit. Ethylene oxide steam containing a light fraction discharged from a column top portion of the light fraction separation column is supplied to the ethylene oxide reabsorption column to recover ethylene oxide.

A column bottom liquid of the light fraction separation column is supplied to an ethylene oxide rectifying column (hereinafter, also simply referred to as a "rectifying column"). Preferably, the rectifying column is provided with a reboiler (not illustrated) for heating at a column bottom portion thereof.

Preferably, the purification is performed at a column bottom temperature of the rectifying column of 35 to 80° C. and a column bottom pressure of the rectifying column of 0.10 to 0.80 MPa gauge, and ethylene oxide steam is obtained from a column top portion of the rectifying column at column top temperature of 2 to 75° C. and a column top pressure of 0.10 to 0.80 MPa gauge. Then, ethylene oxide is liquefied using a rectifying column condenser (not illustrated), and is extracted as product ethylene oxide (EO), while a part thereof is supplied to a column top portion of the rectifying column through a conduit as a reflux liquid.

Note that a column bottom liquid of the rectifying column is extracted through a conduit, if necessary, for separation of heavy components of high-boiling impurities such as acetaldehyde, water, acetic acid, and the like.

<<Ethylene Glycol System>>

In the process for producing ethylene oxide and ethylene glycol illustrated in FIG. 1, a product gas obtained by gas phase oxidation of ethylene using molecular oxygen in the presence of a silver-based catalyst is introduced into the ethylene oxide absorption column and subjected to a contact absorption treatment with water to obtain an ethylene oxide aqueous solution as a column bottom liquid. By-products such as a low molecular weight polymer of ethylene oxide (such as dioxane), ethylene glycol which is a reaction product of ethylene oxide and water, and the like, and a reaction product of ethylene oxide and impurities are contained in the ethylene oxide aqueous solution. As described above, the ethylene oxide aqueous solution is introduced into the ethylene oxide stripping column, and ethylene oxide is stripped from the aqueous solution by heating a column bottom portion of the ethylene oxide stripping column with heated steam, thereby obtaining stripped steam containing ethylene oxide from a column top of the stripping column. The stripped steam contains low-boiling impurities such as formaldehyde and the like and high-boiling impurities such as acetaldehyde, acetic acid, and the like, in addition to ethylene oxide, water, carbon dioxide, and an inert gas (nitrogen, argon, methane, ethane, or the like). Therefore, the stripped steam is subjected to each of a dehydration step, a light fraction separation step, and the like, thereby obtaining purified ethylene oxide.

In this case, an aqueous solution containing substantially no ethylene oxide obtained from the column bottom portion of the ethylene oxide stripping column is circulated and used as an absorption liquid supplied to the ethylene oxide absorption column. However, a part of the aqueous solution obtained from the column bottom portion of the ethylene oxide stripping column (column bottom liquid) is extracted and introduced into the ethylene glycol system. In the present specification, the aqueous solution partially extracted from the column bottom liquid of the stripping column and supplied to the ethylene glycol system is EO discharged water 1. Specifically, a part of the aqueous solution obtained from the column bottom portion of the ethylene oxide stripping column (EO discharged water 1) is concentrated in the by-produced ethylene glycol concentration column and then is preferably introduced into a dehydrating column of the ethylene glycol system. The aqueous solution obtained from the column bottom portion of the ethylene oxide stripping column contains monoethylene glycol as a main component, diethylene glycol, triethylene glycol, and the like, and also contains impurities contained in the ethylene oxide aqueous solution, such as dioxane and the like.

On the other hand, the ethylene oxide aqueous solution obtained by mixing water with the column bottom liquid from the light fraction separation column is fed to the EG reactor whose temperature is constantly kept. A reaction temperature is not particularly limited, but is, for example, 150 to 180° C. A reaction pressure is also not particularly limited, but is, for example, 2.5 MPa or less. A concentration of the ethylene oxide aqueous solution is adjusted with water so that a desired ratio of EG is obtained, and reaction heat is recovered by raising of a temperature of a reaction liquid. A ratio of mono-EG is increased and di- and tri-EG produced as a by-product are reduced as an EO concentration in the reaction liquid is reduced, but the EO concentration in the reaction liquid is generally 9 to 13 mass %, from the viewpoint of preventing energy for removing water from increasing too much. Most of water is recovered in a multi-effect can and circulated and used in the EG reactor. Steam from the ethylene oxidation reactor in the ethylene oxide reaction system can be used as a heat source.

A concentrated EG aqueous solution taken out from the multi-effect can is mixed with by-produced EG concentrated in the by-produced ethylene glycol concentration column to remove moisture in the dehydrating column. An operation condition of the dehydrating column is not particularly limited, but a pressure is, for example, 50 to 500 hPa, and preferably 90 to 120 hPa. A column top temperature is, for example, 30 to 80° C., and preferably 40 to 55° C. A column bottom temperature is, for example, 80 to 120° C., and preferably 90 to 110° C.

In this case, discharged water containing water and ethylene glycol from the steam obtained from the column top of the dehydrating column is distilled and supplied to the by-produced ethylene glycol concentration column as EG discharged water.

Then, an ethylene glycol liquid containing substantially no moisture is obtained from the column bottom portion of the dehydrating column. The ethylene glycol liquid is sequentially rectified in a monoethylene glycol rectifying column (mono-EG rectifying column), a diethylene glycol rectifying column (di-EG rectifying column), and a triethylene glycol rectifying column (tri-EG rectifying column) to obtain each of purified ethylene glycols. Poly-EG of tetra-EG or higher is discharged from a column bottom of the tri-EG rectifying column.

Distillation in the monoethylene glycol rectifying column is performed preferably at 10 to 70 hPa, and more preferably at 25 to 75 hPa, and performed at a column top temperature of preferably 85 to 125° C., and more preferably 100 to 120° C. Distillation in the diethylene glycol rectifying column is performed preferably at 10 to 550 hPa, and more preferably at 15 to 70 hPa, and performed at a column top temperature of preferably 125 to 225° C., and more preferably 135 to 195° C. Distillation in the triethylene glycol rectifying column is performed preferably at 10 to 220 hPa, and more preferably at 10 to 22 hPa, and performed at a column top temperature of preferably 159 to 230° C., and more preferably 159 to 177° C.

(By-produced ethylene glycol concentration step) As described above, a part of the absorption liquid circulating between the absorption column and the stripping column is extracted from the column bottom portion of the stripping column. The column bottom liquid of the stripping column is extracted through a conduit and supplied to the by-produced ethylene glycol concentration step (EO discharged water 1).

In addition, it is preferable that a part of the column bottom liquid of the dehydrating column is subjected to an ethylene glycolation (EG) treatment and then supplied to the by-produced ethylene glycol concentration step (EO discharged water 2). That is, in a preferred embodiment of the present invention, the method includes a step of supplying, to a dehydrating column, an aqueous solution obtained by condensing the steam containing ethylene oxide obtained from the column top portion of the ethylene oxide stripping column, introducing, into a light fraction separation column, a fraction obtained by condensing steam having a high concentration of ethylene oxide obtained from a column top portion of the dehydrating column, and heating a column bottom liquid of the light fraction separation column to separate a light fraction, and the method includes a step of supplying a part of discharged water discharged from a column bottom portion of the dehydrating column to the by-produced ethylene glycol concentration column. Preferably, a part of the discharged water discharged from the column bottom portion of the dehydrating column (column bottom liquid) is subjected to an EG treatment and then supplied to an ethylene glycol concentration column. An example of the EG treatment can include a step of reacting ethylene oxide with water to obtain an aqueous solution containing monoethylene glycol, diethylene glycol, triethylene glycol, tetraethylene glycol, and polyethylene glycol.

In the ethylene glycol concentration step, the column bottom liquid of the stripping column (EO discharged water 1), EO discharged water 2, $CO_2$ discharged water, and EG discharged water are preferably supplied to the by-produced ethylene glycol concentration column. Then, while recovering ethylene glycol concentrated in the by-produced ethylene glycol concentration column through the purification step, 1,4-dioxane is removed from water containing a trace amount of organic matter generated by the concentration, and the water is discharged as discharged water in which a content of 1,4-dioxane is sufficiently reduced.

In the method of producing ethylene oxide and ethylene glycol of the present invention, a divided wall distillation column is used as the by-produced ethylene glycol concentration column.

In a case where a plate column is used as the by-produced ethylene glycol concentration column, ethylene glycol in a feed liquid supplied to the by-produced ethylene glycol concentration column is concentrated in the plate column, and the concentrated liquid is extracted from a column bottom. In this case, water containing a trace amount of organic matter generated by the concentration operation is extracted from a column top. 1,4-dioxane is contained in the organic matter in a column top liquid which is water containing a trace amount of organic matter. In the related art, a concentration of the organic matter in the column top liquid is reduced with activated sludge, and then the column top liquid is discharged as discharged water. However, in order to set a concentration of 1,4-dioxane in the discharged water to 0.5 mg/L or less, it is insufficient to perform only the treatment with the activated sludge.

Meanwhile, by using a divided wall distillation column, 1,4-dioxane can be concentrated in the column. Therefore, the 1,4-dioxane concentrated liquid can be extracted and subjected to a combustion treatment in a waste liquid combustion device. Therefore, the concentration of 1,4-dioxane in the discharged water from the by-produced ethylene glycol concentration column can be 0.5 mg/L or less.

A specific form of the divided wall distillation column is not particularly limited, but a known form can be appropriately adopted.

Figure 2:
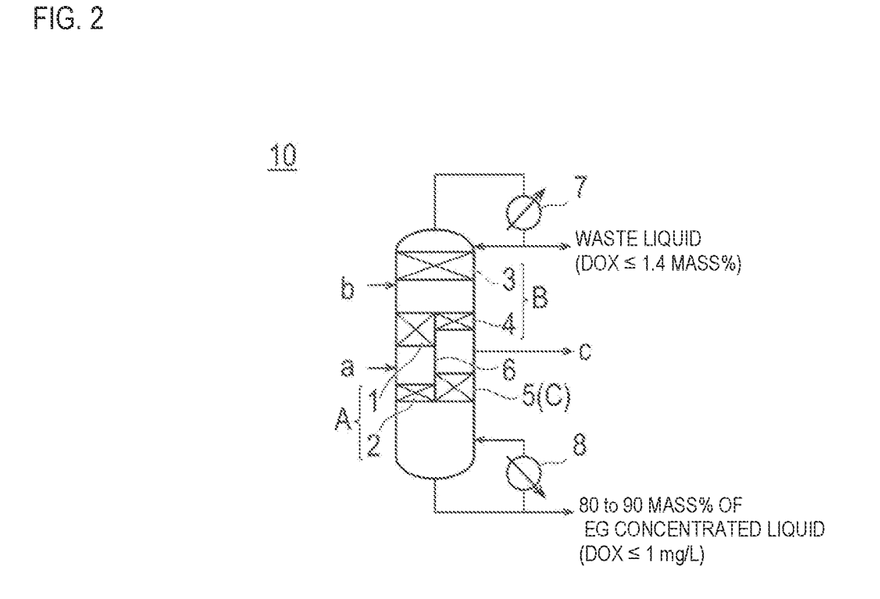
FIG. 2 is a view illustrating an outline of an ethylene glycol concentration column.

FIG. 2 illustrates an outline of a divided wall distillation column 10 used as the ethylene glycol concentration column in an embodiment of the present invention.

The divided wall distillation column 10 has a first distillation section A, a second distillation section B, and a third distillation section C. The first distillation section A includes a concentration portion 1 for concentrating low-boiling and medium-boiling components above a feed a, and includes a recovery portion 2 for recovering low-boiling and medium-boiling components below the feed a. The second distillation section B includes a concentration portion 3 for concentrating a low-boiling component and a recovery portion 4 for recovering a low-boiling component. The third distillation section C includes a concentration portion 5 for concentrating a medium-boiling component.

In the divided wall distillation column 10, the concentration portion 1 and the recovery portion 4 are adjacent to each other and partitioned via a partition 6 in a vertical direction, and the recovery portion 2 and the concentration portion 5 are adjacent to each other and partitioned via the partition 6 in the vertical direction. The recovery portion 4 and the concentration portion 5 are communicated with each other and connected to each other in the vertical direction, and a discharge port c is formed at the connection portion. Furthermore, the concentration portion 3 is communicated with an upper portion of the concentration portion 1 and connected to the upper portion of the concentration portion 1 in the vertical direction.

Here, it is preferable that each of the distillation sections A, B, and C is filled with a filler to form a packed column.

Note that a distillation apparatus is preferably constituted by the divided wall distillation column 10, a condenser 7, a reboiler 8, and the like.

When a feed liquid containing EG, water, and 1,4-dioxane is introduced from the feed a of such a divided wall distillation column 10, the feed liquid is distilled in the first distillation section A and separated into low-boiling and medium-boiling components containing 1,4-dioxane and water, and medium-boiling and high-boiling components containing water and EG.

The low-boiling component containing 1,4-dioxane can be distilled in the second distillation section B, and 1,4-dioxane which is a low-boiling component can be extracted from a column top. This is a waste liquid containing 1,4-dioxane. For example, the waste liquid can be subjected to a combustion treatment in a waste liquid treatment facility. In addition, discharged water in which the 1,4-dioxane component is reduced can be taken out through the discharge port c. In this case, 1,4-dioxane of the low-boiling component is extracted from the column top portion, for example, even in a case where the same heat load is applied, compared to the distillation operation using a non-divided wall column such as a plate column or the like, a concentration of 1,4-dioxane in the discharged water can be reduced, and can be set to a level below the environmental standard value.

The high-boiling component containing EG can be distilled in the third distillation section C, and an ethylene glycol concentrated liquid can be extracted from the column bottom.

Note that in a case where a plurality of feed liquids having different concentrations of ethylene glycol which is a high-boiling component are supplied to the by-produced ethylene glycol concentration column, supply positions of these feed liquids preferably vary depending on the concentration of ethylene glycol in the feed liquid. For example, as illustrated in FIG. 2, a feed b is provided above the first distillation section A and below the concentration portion 3 for the low-boiling component of the second distillation section B. Then, distillation can be more efficiently performed by supplying from the feed b a supply liquid having a smaller amount of the high-boiling component than a supply liquid supplied to the feed a. As a result, the amount of steam required for separation can be reduced.

A supply liquid derived from an ethylene oxide production facility can be used as the feed liquid. Here, as the supply liquid derived from the ethylene oxide production facility, a part of the column bottom liquid of the ethylene oxide stripping column (EO discharged water 1) is used, but it is preferable that discharged water obtained after a part of the column bottom liquid of the dehydrating column is subjected to an ethylene glycolation (EG) treatment (EO discharged water 2) is also used. The supply liquid derived from the ethylene oxide production facility (EO discharged water 1 and EO discharged water 2) contains ethylene oxide and 1,4-dioxane which are low-boiling components, water which is a medium-boiling component, and ethylene glycol which is a high-boiling component. In an embodiment, the supply liquid derived from the ethylene oxide production facility contains 10 to 12 mass % of ethylene glycol, and a content of 1,4-dioxane is 43 mg/L or less.

Furthermore, discharged water discharged from the carbon dioxide gas recovering step described above ($CO_2$ discharged water) may be directly fed to activated sludge so as to treat 1,4-dioxane, but a step of supplying a part of the $CO_2$ discharged water to the by-produced ethylene glycol concentration column is preferably included. Since the $CO_2$ discharged water generated in the carbon dioxide gas recovering step also contains 1,4-dioxane, it is required to perform a treatment for reducing the concentration of 1,4-dioxane before the $CO_2$ discharged water is discharged to the outside of the system. Therefore, the treatment of 1,4-dioxane can be integrally performed by supplying the $CO_2$ discharged water to the ethylene glycol concentration column, and performing the ethylene glycol concentration step, in addition to the EO discharged water 1 (further, EO discharged water 2). The $CO_2$ discharged water is not particularly limited, but is preferably discharged water in which a content of ethylene glycol is less than 1 mass %, and a content of 1,4-dioxane is 20 mg/L or less.

Similarly, the discharged water discharged from the ethylene glycol system or the discharged water derived from the ethylene glycol system (EG discharged water) may be directly fed to activated sludge in order to treat 1,4-dioxane, but a step of supplying the EG discharged water to the by-produced ethylene glycol concentration column is preferably included. Since the EG discharged water generated in the ethylene glycol system also contains 1,4-dioxane, it is required to perform a treatment for reducing the concentration of 1,4-dioxane before EG discharged water is discharged to the outside of the system. Therefore, the treatment of 1,4-dioxane can be integrally performed by supplying the EG discharged water to the ethylene glycol concentration column, and performing the ethylene glycol concentration step, in addition to the EO discharged water 1 (further, EO discharged water 2 and/or $CO_2$ discharged water). Furthermore, by-produced ethylene glycol can be efficiently recovered. The EG discharged water is not particularly limited, but is preferably discharged water in which a content of ethylene glycol is less than 1 mass %, and a content of 1,4-dioxane is 20 mg/L or less. In this case, as the discharged water discharged from the ethylene glycol system (EG discharged water), discharged water generated in the ethylene glycol purification step of purifying concentrated ethylene glycol is preferably used. An example of the ethylene glycol purification step of purifying concentrated ethylene glycol can include a purification step using the EG reactor, multi-effect can, dehydrating column, mono-EG rectifying column, di-EG rectifying column, tri-EG rectifying column, or the like. Discharged water obtained in one or more of these steps can be used in combination. Preferably, discharged water containing water and ethylene glycol distilled from steam obtained from the column top of the dehydrating column by introducing the concentrated ethylene glycol into the dehydrating column is used as the EG discharged water.

As such, the method according to an embodiment of the present invention further includes the ethylene glycol purification step of purifying concentrated ethylene glycol, and a part of the discharged water generated in the ethylene glycol purification step is supplied to the by-produced ethylene glycol concentration column.

An operation condition for the by-produced ethylene For example, a column top pressure is −0.076 to 0.15 MPa gauge, and preferably −0.070 to 0.11 MPa gauge. A column top temperature is, for example, 65 to 130° C., and preferably 70 to 125° C. In addition, a column bottom temperature is, for example, 83 to 170° C., and preferably 89 to 158° C. A concentration of ethylene glycol at the column bottom is, for example, 80 to 90 mass %, and preferably 82 to 88 mass %.

Preferably, the feed liquid is supplied to the by-produced ethylene glycol concentration column 10 from the feed a at the middle of a division portion which is a column side portion. In a case where a plurality of feed liquids are used, at least one feed liquid is preferably supplied from the feed a.

A concentration of ethylene glycol in the column bottom liquid is, for example, 80 to 90 mass %, and preferably 82 to 88 mass %. In addition, a concentration of 1,4-dioxane in the column bottom liquid is, for example, 1 mg/L or less, and preferably 0.1 mg/L or less.

A part of the column bottom liquid discharged from the column bottom of the by-produced ethylene glycol concentration column passes through the heat exchanger, is circulated to the by-produced ethylene glycol concentration column, and is supplied to the dehydrating column of the ethylene glycol system.

This time, as a result of investigating a composition of discharged water containing 1,4-dioxane, it was found that an introduction location of the discharged water to the divided wall distillation column may be changed because it was found that the composition in the discharged water was different. In particular, it was found that in the discharged water generated in the ethylene glycol purification step or the discharged water generated in the carbon dioxide gas system, since a content of ethylene glycol in the discharged water is low, the discharged water can be fed to a distribution portion positioned above the division portion, and as a result of actually changing the introduction location, a running cost can be remarkably reduced.

A low-boiling component containing 1,4-dioxane is concentrated and discharged from the column top portion of the by-produced ethylene glycol concentration column as a column top liquid, the column top liquid is fed to the heat exchanger through a conduit, and a part of the column top liquid is refluxed to the column top portion of the by-produced ethylene glycol concentration column through a conduit. The concentrated liquid discharged from the column top portion of the by-produced ethylene glycol concentration column can be combined with discharged water of another system, if necessary, and can be treated in a waste liquid combustion facility.

When discharged water containing ethylene oxide, ethylene glycol, and 1,4-dioxane is supplied to and distilled in the divided wall distillation column, ethylene oxide and 1,4-dioxane which are low-boiling components can be concentrated and extracted from the column top portion, and ethylene glycol which is a high-boiling component can be concentrated and extracted from the column bottom portion. Since the low-boiling component is extracted from the column top portion, the low-boiling component in the discharged water from the column side portion can be reduced.

Meanwhile, when a plate column is used, the low-boiling component is extracted from the column top portion as discharged water together with water having a medium boiling point, and the high-boiling component is extracted from the column bottom portion. For example, a concentration of 1,4-dioxane (DOX) in the discharged water extracted from the column top liquid is 31.1 mg/L.

Therefore, in a case where the same heat load is applied, when the divided wall distillation column is used, since the low-boiling component containing 1,4-dioxane is extracted from the column top portion, a concentration of the low-boiling component contained in the discharged water can be reduced, and 1,4-dioxane contained in the discharged water can be 0.5 mg/L or less. That is, in a preferred embodiment of the present invention, a concentration of 1,4-dioxane in the discharged water discharged from the column side portion of the by-produced ethylene glycol concentration column is 0.5 mg/L or less. The concentration of 1,4-dioxane in the discharged water is more preferably 0.2 mg/L or less, and still more preferably 0.12 mg/L or less. The concentration of 1,4-dioxane in the discharged water discharged from the by-produced ethylene glycol concentration column can be measured by gas chromatography analysis.

For example, a part of the discharged water obtained as described above in which the content of 1,4-dioxane is 0.5 mg/L or less is returned to the ethylene oxide production step, and a residue is subjected to an activated sludge treatment to reduce a concentration of organic matters, is combined with discharged water of another system, and then is discharged to the outside of the system as final discharged water. Here, from the viewpoint of complying with the water pollution law, a concentration of 1,4-dioxane of the final discharged water is required to be 0.5 mg/L or less, but is preferably 0.2 mg/L or less, more preferably 0.12 mg/L or less, and particularly preferably 0.1 mg/L or less.

In a case where a large amount of organic matters are discharged into the sea, water pollution problems such as red tide and the like are induced, which may cause generation of bacteria or odor. Therefore, in a case where industrial discharged water is discharged to the outside of the system, a concentration of organic carbon is required to be equal to or less than the acceptable value (according to Water Pollution Control Law and regulations). The activated sludge treatment is a treatment for decomposing the organic matters in the discharged water to a carbon dioxide gas or the like to reduce the concentration of the organic matters. For example, a method described in "Introduction of pollution for pollution control managers" by Masao Shitara (Ohmsha, Ltd., 1971) or the like can be adopted.

Note that a concentration of a total organic carbon (TOC) in the discharged water discharged from the column side portion of the by-produced ethylene glycol concentration column is preferably 200 mass ppm or less, from the viewpoint of protecting sludge bacteria. The TOC concentration in the discharged water discharged from the by-produced ethylene glycol concentration column can be measured by combustion oxidation type total organic carbon analysis.

EXAMPLES

Hereinafter, the embodiment of the present invention will be described in more detail using Examples. However, the technical scope of the present invention is not limited only to the following embodiment.

Comparative Example 1

Figure 3:
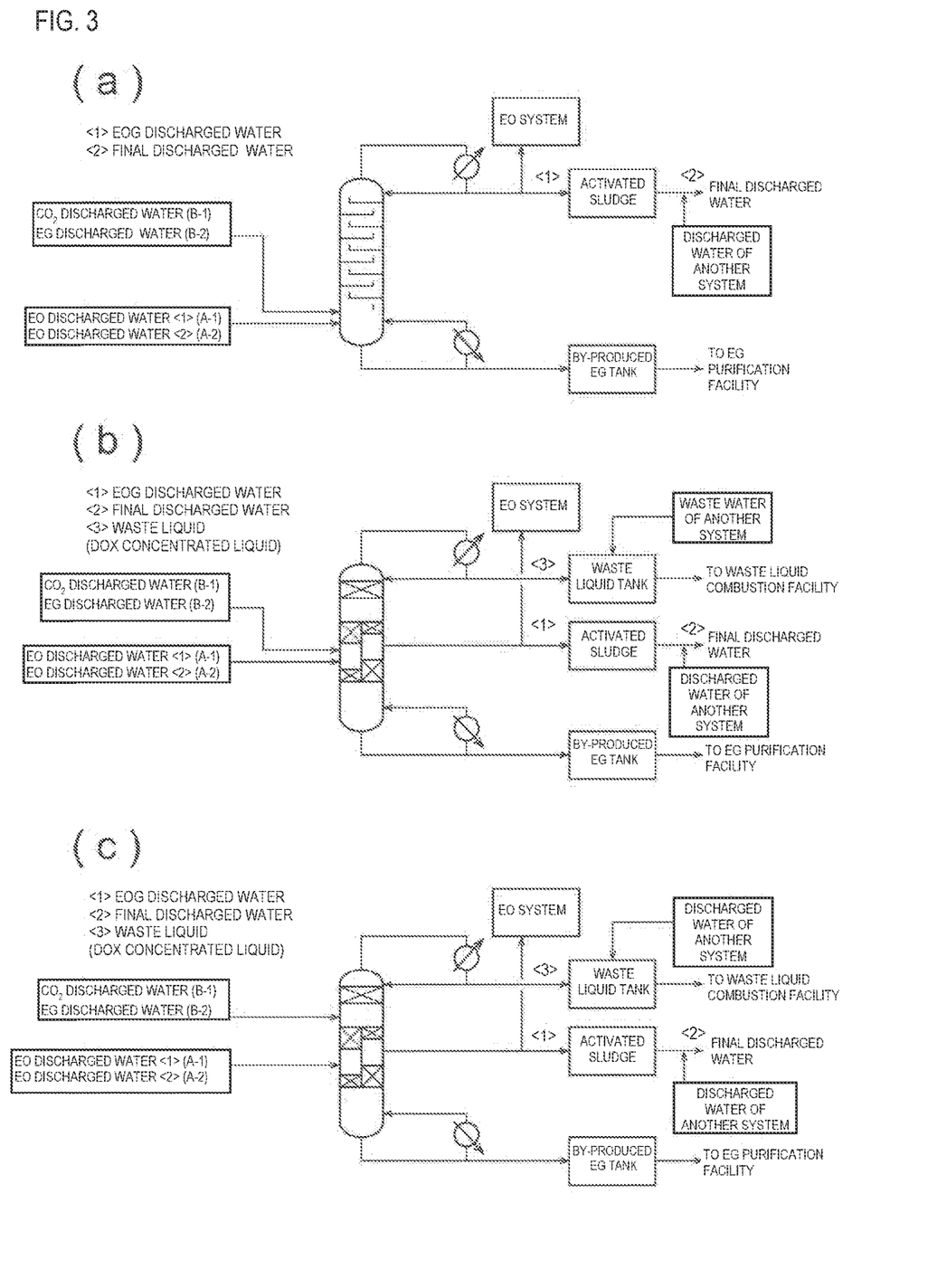
FIG. 3 is a block diagram illustrating a configuration of a production process adopted in each of Examples and Comparative Example.

Ethylene oxide was produced by a process for producing ethylene oxide illustrated in FIG. 1, and by-produced EG was concentrated as illustrated in FIG. 3(a). Note that four systems of a feed liquid to a by-produced EG concentration column are present. That is, the feed liquid to the by-produced EG concentration column includes EO discharged water 1 and 2, $CO_2$ discharged water, and EG discharged water in FIG. 1. In addition, the EO discharged water 1 is obtained by extracting a part of a column bottom liquid of a stripping column, the EO discharged water 2 is obtained by subjecting a column bottom liquid of a dehydrating column to an EG treatment, the $CO_2$ discharged water is a liquid extracted from a $CO_2$ absorption column, and the EG discharged water is discharged water generated in an ethylene glycol purification step of purifying concentrated ethylene glycol. In addition, two systems of the four systems of the feed liquid to the by-produced EG concentration column are derived from an EO system, and the rest is derived from a carbon dioxide gas system and an EG system. Here, the discharged water of the four systems are classified into two systems which are described as a "A" system containing a high concentration of EG (two EO system-derived discharged water) and a "B" system containing a low concentration of EG (carbon dioxide gas system-derived discharged water and EG system-derived discharged water). That is, the A system discharged water is obtained by combining the EO discharged water 1 (A-1) and the EO discharged water 2 (A-2) with each other, and the B system discharged water is obtained by combining the $CO_2$ discharged water (B-1) and the EG discharged water (B-2). As a composition of the A system discharged water, 1,4-dioxane, water, and EG were contained in amounts of 0.0023 mass %, 87.4 mass %, and 12.6 mass %, respectively, and as a composition of the B system discharged water, 1,4-dioxane, water, and EG were contained in amounts of 0.0015 mass %, 99.2 mass %, and 0.043 mass %, respectively. As a result of analyzing the composition, 1,4-dioxane was also contained in the B system discharged water.

Therefore, it was required to treat 1,4-dioxane contained not only in the A system discharged water but also in the B system discharged water. Thus, an attempt was carried out to simultaneously treat both A and B discharged water.

A plate column was used as the by-produced EG concentration column. An operation pressure was 0.11 MPaG, a column top temperature was 122° C., a column bottom temperature was 155° C., and a column bottom EG concentration was 85 mass %. Both feeds A and B were fed to a column bottom portion of the by-produced EG concentration column. In addition, an extraction line was provided at each of the column top and the column bottom, EOG discharged water which was organic matter-containing water containing 1,4-dioxane and a by-produced EG concentrated liquid were extracted from the column top and the column bottom, respectively. A concentration of 1,4-dioxane in the EOG discharged water at this time was 31.1 mg/L. In addition, a TOC concentration in the EOG discharged water was 190 mass ppm. Note that the EOG discharged water refers to discharged water extracted from the by-produced ethylene glycol concentration column, and specifically, refers to discharged water which is obtained by introducing the EO discharged water 1, the EO discharged water 2, the EG discharged water, and the $CO_2$ discharged water to the by-produced ethylene glycol concentration column, cutting by-produced ethylene glycol, 1,4-dioxane, or the like, and is then fed to activate-sludge. In addition, the amounts of discharged water of A system and B system treated were as follows: A1 system: 230 m³ per day, A2 system: 50 m³ per day, B1 system: 30 m³ per day, and B2 system: 50 m³ per day.

Here, the concentration of 1,4-dioxane in the EOG discharged water is calculated by 1,4-dioxane concentration [mg/L]=mass [mg] of 1,4-dioxane in EOG discharged water/volume [L] of EOG discharged water.

The concentration of 1,4-dioxane was determined by the following method and condition.

---

Figure 4:
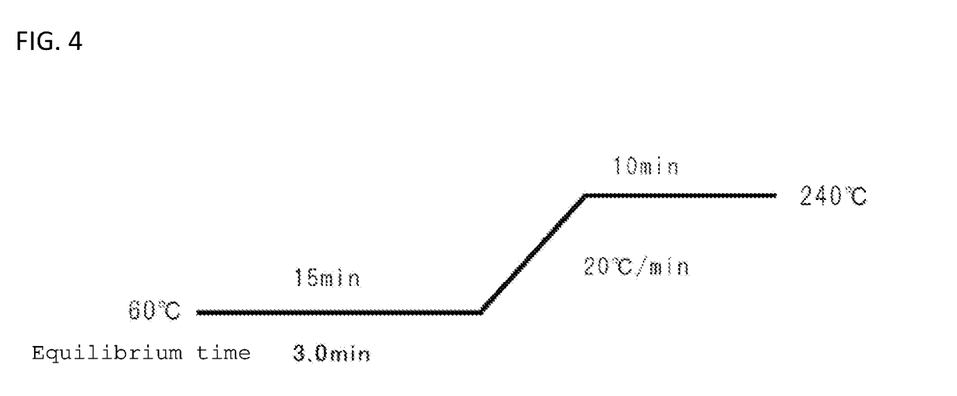
FIG. 4 shows a temperature increasing condition in 1,4-dioxane measurement method in Comparative Example 1.

1,4-Dioxane measurement method
1. Device, tool
(1) Gas chromatography
GC-2010Plus + hydrogen flame ionization detector (FID detector), manufactured by Shimadzu Corporation
Used gas:   He gas (carrier)       $N_2$ gas (make up gas)
            Hydrogen gas (for FID)   Air (for FID)
(2) Auto sampler AOC-20i, manufactured by Shimadzu Corporation
(3) Data processing software LabSolution ver. 5.57 SP1, manufactured by Shimadzu Corporation
(4) Capillary column DB-WAXETR 0.32 mm I.D. × 50 m × 1 µm Film, manufactured by Agilent J&W
2. Reagent
(1) Reagent Special grade       1,4-dioxane
(2) Pure water Distilled and condensed water
3. Measurement and device setting condition
(1) A specified amount of each supply gas is allowed to flow through gas chromatography.
Hydrogen gas: 40 ml/min  Air: 400 ml/min
(2) The measurement device is adjusted to the following conditions.
Vaporization chamber portion temperature        280° C.
Column constant temperature portion temperature 60° C.
Detector portion (FID) temperature              280° C.
<1> Sample injection amount                     2.0 µL
<2> Column inflow condition
Injection mode           Split mode
Control mode             Linear velocity mode
Pressure                 141.5 kPa
Total flow rate          36.7 ml/min
Column flow rate         3.06 ml/min
Column linear velocity   40 cm/sec
Septum purge flow rate   3.0 ml/min
Split ratio              10
<3> Column temperature increasing condition (FIG. 4)
The initial temperature at the start of measurement is set to 60° C. and held for 15 minutes, after the temperature reaches 240° C. at a temperature increase rate of 20° C./min, the temperature is held for 10 minutes, and then the measurement is terminated.

---

In addition, the TOC concentration in the EOG discharged water is calculated by TOC concentration [mass ppm]=mass [kg] of total organic carbon in EOG discharged water/mass [kg] of EOG discharged water×1,000,000.

The TOC concentration was determined by the following method and condition.

TOC Measurement Method
1. Device, tool
Online total organic carbon and total nitrogen meter TOCN4100, manufactured by Shimadzu Corporation
2. Measurement principle
Combustion catalytic oxidation/NDIR method ($CO_2$ measurement)
3. IC treatment
Removal by pre-treatment (acidification-aeration treatment)

The amount of steam required in the by-produced ethylene glycol concentration column was 20.2 t/h. The amount of steam required was obtained by an orifice type flow meter.

In addition, a concentration of 1,4-dioxane in the final discharged water obtained after the EOG discharged water was subjected to the activated sludge treatment was 2.02 mg/L. As shown in the results, it was found that the concentration of 1,4-dioxane exceeded 0.5 mg/L which was a discharge standard, resulting in difficulty in simultaneously treating both the A and B discharged water.

Note that the activated sludge treatment was performed with a full scale activated sludge system of the Kawasaki Ukishima plant of Nippon Shokubai Co., Ltd. (10-12 Ukishima-cho, Kawasaki-ku, Kawasaki, Kanagawa). A solids retention time (SRT) was set to two days, and a hydraulic retention time (HRT) was set to one day. In addition, a mixed liquor suspended solid weight (MLSS) in the activated sludge was appropriately adjusted to be about 3,000 to 8,000 mg/L. A dissolved oxygen (DO) was adjusted to 2 to 10 mg/L, a temperature was adjusted to 20 to 30° C., and a pH was adjusted to 6 to 8.

Example 1

In Comparative Example 1, the type of the by-produced EG concentration column was changed to a divided wall distillation column. (FIG. 3(b)) Then, ethylene oxide was produced in the same manner as that of Comparative Example 1 in terms of the treatment amount and the steam amount, and by-produced EG was concentrated. An operation pressure was 0.11 MPaG, a column top temperature was 122° C., a column bottom temperature was 155° C., and a column bottom EG concentration was 85 mass %. Note that a configuration of the facility was set according to the change to the divided wall distillation column so that an extraction position of the EOG discharged water was changed from the column top to a column middle portion and 1,4-dioxane concentrated water is extracted from the column top. Both feeds A and B were fed to the distribution portion at the middle of the division portion of the by-produced EG concentration column. The other conditions were the same as those of Comparative Example 1. A concentration of 1,4-dioxane in the EOG discharged water was 0.11 mg/L or less. In addition, the TOC concentration in the EOG discharged water was 190 mass ppm, and the amount of steam required in the by-produced ethylene glycol concentration column was 20.2 t/h. The concentration of 1,4-dioxane in the final discharged water obtained after the EOG discharged water was subjected to the activated-sludge treatment was 0.090 mg/L or less.

Example 2

In Example 1, the feed positions of the feed A and the feed B of the by-produced EG concentration column were located at different positions. Then, ethylene oxide was produced in the same manner as that of Example 1 in terms of the treatment amount, and by-produced EG was concentrated (FIG. 3(c)). A concentration of 1,4-dioxane in the EOG discharged water was 0.11 mg/L or less. In addition, the TOC concentration in the EOG discharged water was 190 mass ppm, and the amount of steam required in the by-produced ethylene glycol concentration column was 16.9 t/h. The concentration of 1,4-dioxane in the final discharged water obtained after the EOG discharged water was subjected to the activated-sludge treatment was 0.090 mg/L or less.

Example 3

In Example 2, the amount of steam supplied to the by-produced ethylene glycol concentration column was the same as that of Example 1. Then, ethylene oxide was produced in the same manner as that of Example 2 in terms of the treatment amount, and by-produced EG was concentrated. A concentration of 1,4-dioxane in the EOG discharged water was 0.11 mg/L or less. In addition, the TOC concentration in the EOG discharged water was 150 mass ppm. The concentration of 1,4-dioxane in the final discharged water obtained after the EOG discharged water was subjected to the activated-sludge treatment was 0.09 mg/L or less.

Table 1 shows operation conditions at the time of normal operation, concentration of 1,4-dioxane in discharged water, and the amount of steam (the amount of steam required, the use amount of steam) required for the operation of each Example and Comparative Example. In Table 1, the EOG discharged water refers to the liquid extracted from the discharge port c (side cut liquid) in FIG. 2.

TABLE 1

| | | Comparative Example 1 | Example 1 | Example 2 | Example 3 |
|---|---|---|---|---|---|
| By-produced EG concentration column | | Plate column | Divided wall distillation column | Divided wall distillation column | Divided wall distillation column |
| Supply position of feed A | | Column bottom portion | Middle of division portion | Middle of division portion | Middle of division portion |
| Supply position of feed B | | Column bottom portion (at the same position as that of feed A) | Middle of division portion (at the same position as that of feed A) | Middle of division portion (at a position different from that of feed A) | Middle of division portion (at a position different from that of feed A) |
| Concentration of 1,4-dioxane in discharged water | EOG discharged water (mg/L) | 31.1 | ≤0.11 | ≤0.11 | ≤0.11 |
| | Final discharged water (mg/L) | 2.02 | ≤0.09 | ≤0.09 | ≤0.09 |
| | TOC in EOG discharged water (mass ppm) | 190 | 190 | 190 | 150 |
| Amount of steam | Use amount of 0.9 MPaG | 20.2 | 20.2 | 16.9 | 20.2 |

TABLE 1-continued

| | Comparative Example 1 | Example 1 | Example 2 | Example 3 |
|---|---|---|---|---|
| required of steam (t/h) | | | | |

From the results shown in Table 1, according to the present invention, it was found that the concentration of 1,4-dioxane in the discharged water can be reduced to a concentration below the discharged water standard value.

From the comparison between Comparative Example 1 and Example 1, it was found that the concentration of 1,4-dioxane in the EOG discharged water was reduced to 0.1 mg/L or less of Example 1 as compared to 31.1 mg/L of Comparative Example 1, by changing the type of the tower of the by-produced EG concentration column to the divided wall distillation column. In this regard, large auxiliary equipment such as a reboiler and a condenser, which are required to spend expensive manufacturing costs, are not required to be changed from the plate column described in Comparative Example 1. Thus, a construction cost is relatively low, and an installation area is the same as that of Comparative Example 1. In addition, in Example 1, a reduction in concentration of 1,4-dioxane was implemented without an increase in the amount of steam required, compared to Comparative Example 1.

Furthermore, from the comparison between Examples 1 and 2, it was found that the amount of steam required, that is, a running cost was significantly reduced by supplying the feed A containing a high concentration of ethylene glycol and the feed B containing a low concentration of ethylene glycol to different positions, and supplying the feed B to the distribution portion of the divided wall distillation column instead of a general feed position of a liquid. In addition, from the comparison between Examples 2 and 3, it was found that the TOC concentration in the EOG discharged water was reduced by making the running cost the same as before the type of the tower was changed.

The present application is based on the Japanese patent application No. 2018-151727 filed on Aug. 10, 2018, and the disclosed contents thereof are referred to and incorporated here as a whole.

REFERENCE SIGNS LIST 1, 3, 5 concentration portion
2, 4 recovery portion
6 partition
7 condenser
8 reboiler
10 divided wall distillation column
A, B, C distillation section
a, b feed
c discharge port

The invention claimed is:
1. A method of producing ethylene oxide and ethylene glycol, the method comprising:
a step of producing ethylene oxide, including
supplying, to an ethylene oxide absorption column, a reaction product gas containing ethylene oxide and generated in an ethylene oxidation reaction step in which ethylene is subjected to catalytic gas phase oxidation using a molecular oxygen-containing gas in the presence of a silver catalyst,
bringing the reaction product gas into contact with an absorption liquid supplied to the ethylene oxide absorption column,
supplying a column bottom liquid of the ethylene oxide absorption column, which contains ethylene oxide, to an ethylene oxide stripping column, and
obtaining steam containing ethylene oxide from a column top portion of the ethylene oxide stripping column by heating a column bottom portion of the ethylene oxide stripping column;
a step of extracting a part of a column bottom liquid of the ethylene oxide stripping column and supplying the extracted column bottom liquid to a by-produced ethylene glycol concentration column as a first ethylene oxide (EO) discharged water;
a step of supplying, to a dehydrating column, an aqueous solution obtained by condensing the steam containing ethylene oxide obtained from the column top portion of the ethylene oxide stripping column, introducing, into a light fraction separation column, a fraction obtained by condensing steam having a high concentration of ethylene oxide obtained from a column top portion of the dehydrating column, and heating a column bottom liquid of the light fraction separation column to separate a light fraction, wherein a part of discharged water discharged from a column bottom portion of the dehydrating column is subjected to an ethylene glycolation (EG) treatment and supplied to the by-produced ethylene glycol concentration column as a second EO discharged water;
a carbon dioxide gas recovering step of supplying at least a part of a carbon dioxide-containing gas discharged from a column top portion of the ethylene oxide absorption column to a carbon dioxide gas absorption column, extracting a carbon dioxide gas-rich absorption liquid obtained by bringing the carbon dioxide-containing gas into contact with an absorption liquid as a column bottom liquid of the carbon dioxide gas absorption column and supplying the extracted carbon dioxide gas-rich absorption liquid to an upper portion of a carbon dioxide gas stripping column, and stripping a carbon dioxide gas from the carbon dioxide gas-rich absorption liquid and discharging the carbon dioxide gas from a column top portion of the carbon dioxide gas stripping column as an exhaust gas, wherein discharged water discharged from the carbon dioxide gas recovering step is supplied to the by-produced ethylene glycol concentration column as a $CO_2$ discharged water;
an ethylene glycol purification step of purifying concentrated ethylene glycol, wherein a part of discharged water generated in the ethylene glycol purification step is supplied to the by-produced ethylene glycol concentration column as an EG discharged water; and
a step of concentrating ethylene glycol produced as a by-product in the step of producing ethylene oxide, and distilling and separating 1,4-dioxane produced as a by-product in the step of producing ethylene oxide, wherein the by-produced ethylene glycol concentration column is a divided wall distillation column, and wherein a supply position of a feed liquid containing the first EO discharged water and the second EO discharged water and a supply position of a feed liquid containing the $CO_2$ discharged water and EG discharged water supplied to the by-produced ethylene glycol concentration column are different depending on a concentration of ethylene glycol in the feed liquids.

2. The method according to claim 1, wherein a concentration of 1,4-dioxane in discharged water discharged from the by-produced ethylene glycol concentration column is 0.5 mg/L or less.

3. The method according to claim 1, wherein in the by-produced ethylene glycol concentration column, a low-boiling component containing 1,4-dioxane is concentrated at a column top portion, and a concentrated liquid is treated in a waste liquid combustion facility.

* * * * *